United States Patent
Kuchimanchi et al.

(10) Patent No.: US 12,297,479 B2
(45) Date of Patent: May 13, 2025

(54) PRODUCTION OF HIGH PURITY ORGANIC LACTIC ACID AND ITS SALTS AND VARIOUS APPLICATIONS THEREOF

(71) Applicants: Venkata Satya Sarveswara Sairam Kuchimanchi, Secunderabad (IN); Vaishnavi Kuchimanchi, Secunderabad (IN)

(72) Inventors: Venkata Satya Sarveswara Sairam Kuchimanchi, Secunderabad (IN); Vaishnavi Kuchimanchi, Secunderabad (IN)

( * ) Notice: Subject to any disclaimer, the term of this patent is extended or adjusted under 35 U.S.C. 154(b) by 405 days.

(21) Appl. No.: 17/433,067

(22) PCT Filed: Jun. 10, 2020

(86) PCT No.: PCT/IN2020/050513
§ 371 (c)(1),
(2) Date: Aug. 23, 2021

(87) PCT Pub. No.: WO2021/014460
PCT Pub. Date: Jan. 28, 2021

(65) Prior Publication Data
US 2022/0154227 A1 May 19, 2022

(30) Foreign Application Priority Data
Jul. 22, 2019 (IN) .............................. 201941029553

(51) Int. Cl.
*C12P 7/56* (2006.01)
*C12N 1/20* (2006.01)
(52) U.S. Cl.
CPC . *C12P 7/56* (2013.01); *C12N 1/20* (2013.01)
(58) Field of Classification Search
CPC ....................................................... C12P 7/56
See application file for complete search history.

(56) References Cited

U.S. PATENT DOCUMENTS

2014/0287469 A1* 9/2014 Medoff .................... E04B 1/92
435/99

FOREIGN PATENT DOCUMENTS

| CN | 102643876 A | 8/2012 |
| CN | 103781898 A | 5/2014 |

(Continued)

OTHER PUBLICATIONS

Akoetey et al. "The effect of adaptation of Lactobacillus amylovorus to increasing concentrations of sweet potato starch on the production of lactic acid for its potential use in the treatment of cannery waste", 2018, Journal of Environmental Science and Health, Part B, vol. 53, No. 12, p. 802-809 (Year: 2018).*

(Continued)

*Primary Examiner* — Gary B Nickol
*Assistant Examiner* — Amelia Nicole Dickens
(74) *Attorney, Agent, or Firm* — Hamilton, Brook, Smith & Reynolds, P.C.

(57) ABSTRACT

The present invention relates to a novel, time and cost effective, commercially viable and environmentally safe fermentative production process for "High Purity Organic Lactic acid and its Salts and Various Applications in livestock, food and pharma industry as well as acidifier in aqua culture". A microbial consortium of *Lactobacillus plantarum* and *Lactobacillus delbrueckii* cultures with high acid tolerance trait which are developed in-house over a period of one year is used in the fermentation process. Glucose (@ 18-20%), obtained from sweet potato starch, and protein hydrolysate used as the chief sources of carbon and nitrogen, respectively. A novel semi-fed-batch fermentation approach is adopted for maximum lactic acid yield with a purity of 90-92%, which is achieved within 48 hours of fermentation. Following downstream process, the liquid product contained chiefly lactic acid, and small proportions of propionic acid (Continued)

and acetic acid. Further, preparation of calcium, sodium, zinc and potassium salts of lactic acid has been elaborated. The lactic acid and its salts are suited for applications such as organic preservative, livestock nutritional supplement and as active pharmaceutical ingredient as well as acidifier in aqua culture.

13 Claims, 1 Drawing Sheet

(56) References Cited

FOREIGN PATENT DOCUMENTS

| CN | 104673691 A | 3/2015 | |
|---|---|---|---|
| CN | 107173556 A | 9/2017 | |
| CN | 107594135 A | 1/2018 | |
| JP | H 11243867 A | 9/1999 | |
| KR | 20020019992 | 3/2002 | |
| RU | 2250265 C2 | 4/2005 | |
| WO | WO 2001/076391 A1 | 10/2001 | |
| WO | WO-03066816 A2 * | 8/2003 | ............ C12P 19/02 |

OTHER PUBLICATIONS

"Cloth", Dictionary.com, Website archived via the Wayback Machine Jun. 21, 2019. (Year: 2019).*
Cyrs et al. "Nanoparticle collection efficiency of capillary pore membrane filters", 2010, Journal of Aerosol Science, vol. 41, p. 655-664. (Year: 2010).*
"Calcium Lactate Safety Data Sheet", Jun. 6, 2015, JOST, p. 1-6. (Year: 2015).*
"Lactic Acid Safety Data Sheet", print date Dec. 12, 2016, Lab Alley. (Year: 2016).*
Zhang et al. "Lactic acid production from biomass-derived sugars via co-fermentation of Lactobacillus brevis and Lactobacillus plantarum", 2015, Journal of Bioscience and Bioengineering, vol. 119 No. 6, p. 694-699. (Year: 2015).*
Webpage capture from NCIM and ATCC databases for "NCIM 5356", "NCIM 2083", and "ATCC 8014", images captured Apr. 20, 2024 from www.ncl-india.org and www.atcc.org (Year: 2024).*
Anyasi, T.A., et al., "Application of organic acids in food preservation", 2017, book: Organic acids: characteristics, properties and synthesis, Nova Science Publishers. Chapter 1, pp. 1-45.
Dibner J.J., et al., "Use of organic acids as a model to study the impact of gut microflora on nutrition and metabolism". J Appl. Poult. Res. (2002) 11: 453-63.
Dittoe D., et al., "Organic Acids and Potential for Modifying the Avian Gastrointestinal Tract and Reducing Pathogens and Disease", Frontiers in Veterinary Science (2018) 5: 216, 12 pages.
Economou V., et al., "Agriculture and food animals as a source of antimicrobial-resistant bacteria", Infect Drug Resist. (2015) 8:49-61.—Abstract Only.
Jones F.T., et al., "Observations on the history of the development of antimicrobials and their use in poultry feeds", Poult. Sci. (2003) 82(4):613-7.—Abstract Only.
Notification of Transmittal of the International Search Report and the Written Opinion of the International Search Authority, or the Declaration for International Application No. PCT/IN2020/050513, "Production of High Purity Lactic Acid and Its Salts and Various Applications Thereof" date of mailing: Sep. 24, 2020.
Olsen, S.J., et al., "Multidrug-resistant salmonella typhimurium infection from milk contaminated after pasteurization", Emerg. Infect. Dis. (2004) 10(5):932-5.—Abstract Only.
Ricke S.C. "Perspectives on the use of organic acids and short chain fatty acids as antimicrobials", Poult Sci. (2003) 82(4):632-9.—Abstract Only.
Smyser, C.F., et al., "Evaluation of organic acids and other compounds as *Salmonella antagonists* in meat and bone meal", Poult. Sci. (1979) 58:50-4.
Tona, G.O., "Current and Future Improvements in Livestock Nutrition and Feed Resources", Animal Husbandry and Nutrition, Intech Open. (2018), 24 pages, OI: 10.5772/intechopen.73088.
Van Immerseel F, et al., "The use of organic acids to combat *Salmonella* in poulty: a mechanistic explanation of the efficacy", Avian Pathol. (2006) 35:182-8.—Abstract Only.
Van Staden, J.J., et al., The control of bacterial contamination in carcass meal with propionic acid. Onderstepoort J Vet Res. (1980) 47(2):77-82.—Abstract Only.
Zhang, Y. et al., "Lactic acid production from biomass-derived sugars via co-fermentation of *Lactobacillus brevis* and *Lactobacillus plantarum*.", Journal of Bioscience and Bioengineering, (2015) 119(6): 694-699. Abstract Only.

* cited by examiner

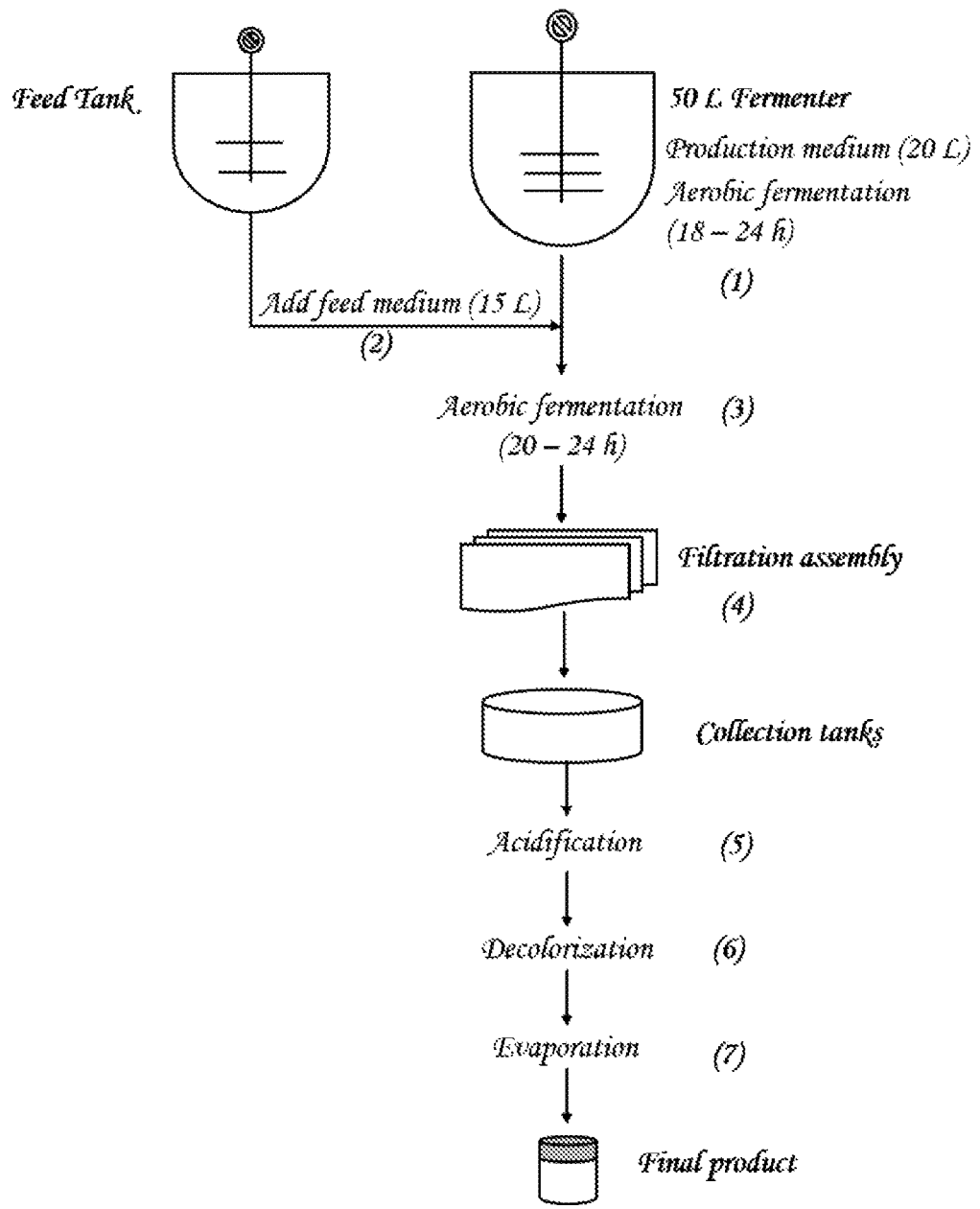

PRODUCTION OF HIGH PURITY ORGANIC LACTIC ACID AND ITS SALTS AND VARIOUS APPLICATIONS THEREOF

This application is the U.S. National Stage of International Application No. PCT/IN2020/050513, filed Jun. 10, 2020, which designates the U.S., published in English, and claims priority under 35 U.S.C. § 119 or 365 (c) to Indian Application No. 201941029553, filed Jul. 22, 2019. The entire teachings of the above applications are incorporated herein by reference.

FIELD OF THE INVENTION

The present invention deals with the High Purity Organic Lactic acid and its Salts, its Production and Various Applications in Food industry, Pharma industry, Livestock and Aqua culture. The high purity organic lactic acid and its salts are produced through a novel semi-fed-batch fermentation technology. It is a clean label and natural product with applications in livestock industry as nutritional supplement for animal growth promotion and disease control as well as in food industries as food preservatives. It acts as an effective antimicrobial component and pH regulator in Aqua culture industry. It is an effective source for acidification of foods like pickles. It can even prevent the growth of pathogenic microbes such as *Escherichia coli, Aspergillus* sp., and even non-classical food borne pathogens such as *Klebsiella pneumoniae*. The salts of Lactic acid were effectively used as a Nutritional supplements as well as base material in pharma industry.

BACKGROUND OF INVENTION

In order to meet the nutritional requirements of the ever-increasing human population, global livestock production has increased substantially over the years, resulting in increased animal population. Consequently, this has put pressure on the limited traditional livestock nutritional resources, thereby severely limiting the quantity and quality of livestock produced (1). To overcome this challenge, scientists are looking for innovative ways to enhance the quality of the most critical input in livestock production—the animal nutritional supplement. Antibiotics have been consistently used as animal growth promoter; however, this has led to development of antibiotic resistance among animals (2-4). Another approach is to incorporate a consortium of chemical-based macro- and micro-nutrients and supplements in animal feed. Although these nutritional supplements have desired efficacy, studies have red flagged long term side effects of these chemically synthesised feed inputs. As such, efforts are being made to introduce biologically synthesised nutrient supplements that have zero side effect and provide long term benefits to the livestock.

Dietary introduction of organic acid—based compounds via nutritional supplements is a promising approach that is quickly gaining importance in the livestock industry. Organic acids such as lactic acid, acetic acid, propionic acid, etc., lower the pH of gastrointestinal tract, improve the activity of proteolytic and lipolytic enzymes, enhance nutrient digestion and absorption, increase digestive enzyme activity, promote growth of beneficial gut microbiota and exhibit bactericidal, bacteriostatic and antifungal properties (5-9). This results in improvement in overall health of livestock and an increase of their nutritional value.

Organic acids, owing to their bactericidal, bacteriostatic and antifungal properties, have also found applications as food preservatives (10, 11). Salts of organic acids are being used as natural preservatives for increasing the shelf-life of bakery products and raw and processed meat products. As substitutes for chemical preservatives, these are natural compounds having no-side effects on human health.

Production of acetic acid, lactic acid, and propionic acid individually by microbial fermentation technology is well reported. Many species of *Acetobacter, Lactobacillus* and *Propionibacterium* are used for the production of these organic acids in controlled conditions. However, for enhanced functionality of the formulation, a combinational production of these organic acids will be an impending alternative. As such, a number of patents have been filed globally relating to different aspects of organic acid fermentative production and applications. Fermentation-based acid production that is of high quality, is commercially viable and is economically safe is a huge challenge. Several methodologies have been outlined in patents claiming to overcome these challenges.

Patent application number CN 201310625005 claims to have used a novel *Lactobacillus plantarum* strain as the effective microorganism for lactic acid synthesis using a variety of carbon sources as substrate (12). The maximum lactic acid yield achieved in the said invention is 68 g/L over process duration of 72 hours, using glucose as the carbon source. In comparison, in the present invention the yield of lactic acid is 72-75 g/L, i.e. 9% higher yield in 33% lesser time. Hence, the present invention is more efficient qualitatively and quantitatively.

Yet another invention, Patent application number CN201210135060.5 claims to increase the lactic acid production efficiency through the use of soybean protein hydrolysate (13). In the present invention lactic acid yield of 32-35 g/L over a process period of 72 hours is achieved. The present invention, in comparison, discloses 53% higher lactic acid yield in 33% lesser process time.

CN 201710917450 has used fermented biological material as feed for livestock (14). Raw materials such as alfalfa, corn stover, barley straw, soybean stover, and sweet sorghum have been used as substrate for fermentation by *Lactobacillus* bacteria. The fermented product is then fortified with minerals to yield the final product, i.e. the livestock feed, which is an undefined mixture containing lactic acid, proteins, carbohydrates, enzymes and probably microorganisms, which exhibit a cumulative effect. The process and product of the present invention, on the other hand, are more defined. Although the microorganism used—Lactic acid bacteria—is common in both, its intended use is different. In the present invention, inventors are using the bacteria to produce lactic acid as the principal active compound which can then be used in various forms as nutritional supplement.

Similar patent applications claiming the use of biological raw materials as substrates for microbial fermentation have been filed. CN 201710307429 describes use of cassava as a substrate and its enzymatic degradation to produce cassava residue which is then fermented using yeast and molds to produce a variety of organic compounds (15). The patent application is significantly different to the present invention. Firstly, in the present invention, sweet potato is used as substrate to extract glucose which has then been used as a carbohydrate source. The medium used in the present invention is 'defined', containing specific amounts of certain nutrients. Secondly, the microorganisms used are different. Third, the final product of the above patent is an undefined mixture containing alcohol, lactic acid, proteins, carbohydrates, enzymes and probably microorganisms, which exhibit a cumulative effect. The process and product of the present invention, on the other hand, are more defined with specific use and mode of action.

Patent no. CN 201280031729 outlines the conversion of silage into fodder using a strain of *Lactococcus* (16). The principal active compound is bacteriocin, nisin, which is produced during the microbial conversion process. Although the end product's applications might be similar to the present invention, however, the execution is significantly different. The substrate used is 'not defined' in the above patent, active component is different and a different genus of lactic acid producing bacteria has been used. The present invention is a more controlled and defined process and product with a wider range of applications and customization possibilities.

RU02250265 relates to production of ethanol with feeding stuffs as a by-product (17). Undefined raw material has been used. Several bacteria with different activities have been used mainly to produce ethanol and in the process also convert the raw material into a mixture of bacteria—degraded proteins, enzymes, amino acids, carbohydrates, etc. that may act as a source of feed for the livestock. The present invention is a specific product with a defined process and a defined mode of action with higher quality.

JP6605198 outline the conversion of silage into fodder using actinomyces and *L. plantarum* (18). Although the end product's applications may be similar to the present invention, the execution is significantly different. The substrate used is undefined with a non-specific mode of action. The present invention is a more controlled and defined process and product with a wider range of applications and customization possibilities.

Patent application no. WO/2001/076391 relates to production of a cultured savoury base as a pet food ingredient produced using a combination of enzymatic protein hydrolysate, an enzyme and a glutaminase-producing *Lactobacillus* strain (19). The invention only acts as a flavouring agent for pet foods with little nutritional benefits. The present invention, on the contrary, contains microbial—synthesized lactic acid and its salts which promote disease resistance and overall health of the consumer. The patent application no. KR1020020019992 relates to an oligopeptide-based salt containing proteins, calcium, Fe, etc. as a food product with increased calcium absorption efficiency (20). In contrast, the present invention, being of microbial origin, has higher purity, a wider range of function and applicability, while being economically viable and environmentally safe to produce.

SUMMARY OF THE INVENTION

The present invention deals with the High Purity Organic Lactic acid and its Salts, its Production and Various Applications in Food industry, Pharma industry, Livestock and Aqua culture. The "high purity organic lactic acid and its salts" is produced through a novel "semi-fed-batch fermentation" of two in-house developed strains—*Lactobacillus delbrueckii* 5356 and *Lactobacillus plantarum* 2083—within batch duration of 40-48 hours. In phase 1 of production, the microbes are grown in an optimized "production medium" for 24 hours, after which an optimized "feed medium" is added to the culture and allowed to incubate for an additional 20-24 hours. The production and feed medium contain high concentrations of glucose, extracted from sweet potato through enzymatic hydrolysis, as carbohydrate source and protein hydrolysate as nitrogen source. The optimized production and feed medium containing high glucose content (18-20%) combined with the novel "semi-fed-batch fermentation" approach and co-fermentation of two high yielding strains results in a product that has high lactic acid content, with a short batch time of 48 hours.

The other embodiment of the present invention relates to the main component of the organic acid produced which is lactic acid with 90-92% purity.

In another embodiment of the present invention, the high purity lactic acid produced can be conveniently converted into salts of sodium, potassium, zinc, magnesium and calcium through modifications in downstream processing and product recovery steps. The acid-salt complexes thus formed have high concentrations of lactic acids and respective elements that improve their quality and range of applications.

The other embodiment of the present invention relates to the wide range of applications of the present product. In livestock industry as a component of nutritional supplement, it can be used as source of vital micro- and macronutrients and to prevent bacterial and fungal diseases in animals. The cumulative effect would be improved overall health of the animal and an increase in its nutritional value. For food and bakery industry, it can be a potent source of natural preservative. Its addition in food preparations like pickles, salads, sauces, beverages, meat and bakery goods can prevent food spoilage. In the case of meat, it will increase the tenderness of the meat besides functioning as an antimicrobial preservative.

BRIEF DESCRIPTION OF DRAWINGS

FIG. 1: Flow chart of the process for high purity organic lactic acid and its salts production.

DETAILED DESCRIPTION OF THE INVENTION

The present invention discloses the process of production of "high purity organic lactic acid and its salts thereof". Two lab-improved strains of *Lactobacillus* spp. were used for microbial conversion of glucose, obtained through enzymatic hydrolysis of sweet potato starch, into lactic acid using a novel semi-fed-batch fermentation process with a batch time of 40-48 hours. Subsequent methodology for fortification with different minerals like calcium, sodium, potassium and zinc to produce different natural organic lactate salts was disclosed.

The microbial consortia comprising two in-house developed acid tolerant strains of *Lactobacillus delbrueckii* and *Lactobacillus plantarum* which were modified by way of strain improvement through media optimization experiments for product yield enhancement at the 'in house R&D section' of Prathista Industries Limited. The bacterial cultures were originally procured as *L. delbrueckii* 5356 and *L. plantarum* 2083 from National Collection for Industrially Important Microorganisms (NCIM), at National Chemical Laboratory, Pune and were further modified by way of strain improvement methods. *Lactobacillus delbrueckii* 5356 was deposited on Sep. 26, 2024, and assigned Accession Number MTCC 25858 and *Lactobacillus plantarum* 2083 was deposited on Sep. 26, 2024, and assigned Accession Number MTCC 25859. These lab-improved strains were deposited under the Budapest Treaty at the Microbial Type Culture Collection & Gene Bank, CSIR-Institute of Microbial Technology, Sector 39-A, Chandigarh 160036 India.

Another embodiment of the present invention relates to high purity lactic acid with 90-92% purity produced from the main carbohydrate source (18-20%) used in media for fermentation obtained from glucose extracted enzymatically from starch of organically cultivated sweet potato. The fermentation process was optimized with different media constituents and controlling parameters. The upstream process was completed when reducing sugars completely exhausted in the fermenter. The downstream process includes the leaf filtration of liquid for obtaining the liquid lactic acid containing 90-92% lactic acid.

In another embodiment of the present invention the fortification of liquid lactic acid with $CaCO_3$ for calcium lactate, with $Na_2CO_3$ for sodium lactate, with $K_2CO_3$ for potassium lactate, with $ZnCO_3$ for zinc lactate or with $MgCO_3$ for magnesium lactate is disclosed. Sodium, calcium, zinc and magnesium lactates are concentrated in evaporation tanks, dried in tray dryers and pulverized to obtain fine powders of respective lactates with lactic acid concentration of 48-51% for sodium lactate, 60-62% for calcium lactate, 61-64% for zinc lactate and 74-75% for magnesium lactate. Potassium lactate is evaporated and filtered to obtain a liquid solution containing 34-36% lactic acid.

The other embodiment of the present invention relates to the wide range of applications of the present product. In livestock industry as a component of nutritional supplement, it can be used as source of vital micro- and macronutrients and to prevent bacterial and fungal diseases in animals. The cumulative effect would be improved overall health of the animal and an increase in its nutritional value. For food and bakery industry, it can be a potent source of natural preservative. Its addition in food preparations like pickles, salads, sauces, beverages, meat and bakery goods can prevent food spoilage. In the case of meat, it will increase the tenderness of the meat besides functioning as an antimicrobial preservative.

The present invention is further explained by the following examples. However, the present invention is not limited to these examples in any manner. The following examples are intended to illustrate the working of disclosure and not intended to take restrictively to apply any limitations on the scope of the present invention. Those persons skilled in the art will understand that the equivalent substitutes to the specific substances described herein, or the corresponding improvements are considered to be within the scope of the invention.

EXPERIMENTAL DETAILS & RESULTS

Example 1

Extraction of Glucose
(A) Preparation of Sweet Potato Starch Hydrolysates

About 100 kg of freshly harvested sweet potato tubers were peeled and pulverized. The resulting mash (approx. 88 kg) was centrifuged to obtain about 38 kg of discharged liquid. The liquid was collected in a settling tank and allowed to stand overnight. The clear solution was decanted leaving the residual raw starch behind.

(B) Enzymatic Hydrolysis of Starch

The solution was mixed with water in 1:2 ratio and cooked for 3-4 hours at 80-85° C. in a cooker tank (1 KL capacity). The resultant viscous solution contained about 10% dry solids. A known quantity of this gelatinized starch solution was taken, and soluble enzymes (α-Amylase and Glucoamylase) were added. The reactions were carried out in stirred tanks at 45° C., pH 4.5 for 72 hours. The resulting solution consists of 95-97% glucose with 3-5% higher disaccharides while the enzyme was removed by heat denaturation at higher temperature.

Example 2

Upstream Process Parameters

Two in-house developed acid tolerant strains of *Lactobacillus delbrueckii* and *Lactobacillus plantarum* originally procured from NCIM (*L. delbrueckii* 5356, *L. plantarum* 2083) were used for two-phase fermentation process. Pre-inoculum (5 L) was prepared using 'seed medium' in a stainless-steel stirred tank reactor (10 L). Fermentation was carried out for 14-17 hours. Temperature and pH were set at 40±2° C. and 6.0±0.2, respectively. Aeration was maintained at 1.5 Kg and impeller speed was set at 150 rpm. The seed medium composition was as follows:

| Components | % w/v |
| --- | --- |
| Sweet potato extract | 12-15 |
| Ammonium sulphate | 0.5 |
| Potassium dihydrogen phosphate | 0.012 |
| Sodium dihydrogen phosphate | 0.2 |
| Magnesium sulphate | 0.02 |
| Calcium carbonate | 4 |
| Zinc sulphate | 0.03 |

Thereafter, the first phase of fermentation process was performed using 'production medium' (20 L) in a stainless steel stirred-tank bioreactor (50 L). Medium was sterilized in-situ, cooled and inoculated with 10% inoculum from the seed culture. Temperature and pH were set at 43±2° C. and 6.0±0.2, respectively. Aeration was maintained at 1.5 kg and impeller speed was set at 200 rpm. The composition of the production medium was as follows:

| Components | % w/v |
| --- | --- |
| Sweet potato extract | 18-20 |
| Protein hydrolysate | 0.50 |
| Potassium dihydrogen phosphate | 0.02 |
| Magnesium sulphate | 0.02 |
| Calcium carbonate | 3 |
| Zinc sulphate | 0.015 |

In phase 2, a 15 L pre-sterilized 'feed medium' was fed to the 24-hour old culture in the 50 L fermenter. The fermentation process was carried out for another 24 hours. pH was set at 5.5±0.2, temperature at 43±2° C., agitation at 200 rpm and aeration at 1.5 Kg. The 'feed medium' composition was as follows:

| Components | % w/v |
| --- | --- |
| Sweet potato extract | 11-16 |
| Protein hydrolysate | 0.35 |
| Yeast extract | 0.2 |
| Potassium dihydrogen phosphate | 0.01 |
| Magnesium sulphate | 0.02 |

The pH of the medium during the entire fermentation process was maintained by adding sterile carbonate salts of sodium, calcium, potassium, etc., based on end product specifications.

Example 3

In-Process Monitoring of Microbial Growth, Glucose Consumption and Product Yield The cell growth during fermentation was measured in terms of optical density using UV-Vis spectrophotometer at a wavelength of 600 nm, in 3 mL of cuvettes. For dry cell weight estimation, 10-15 mL of fermentation broth was centrifuged at 10,000 rpm for 10 min in a pre-weighed empty falcon tube and dried at 60° C. under vacuum till constant weight was achieved. The dry weight of cells was calculated from the substitution of final falcon weight containing cells with the pre-weighed empty falcon weight.

Glucose consumption in terms of residual sugar concentration in fermentation broth was periodically monitored through wet analysis procedure. Lactic acid yield was analysed in in-process samples as well as finished product samples by High-Performance Liquid Chromatography (HPLC) based method. Analysis of organic acid content involved initial sample preparation, analysis and calculations. 0.1 g of test sample was dissolved in 100 mL of HPLC water. Degassing was performed with an ultra-sonicator to prepare the test sample vials. Further, the sample was filtered with a sterile 0.2 μm PTFE filter (Axiva® 200050 RI, AXIVA Sichem Biotech Pvt. Ltd., India). The samples were analyzed with reference to analytic reference standards of respective organic acids.

Further, samples were analyzed by injecting 20 μL of the prepared samples into the HPLC (Shimadzu LC2030 CHT) system. Organic acids column (250×4.6 mm) was used by maintaining column temperature at 30° C. against 8 mM sulfuric acid in water mobile phase. The flow rate was maintained at 0.5 mL/min. while the total run time was 35 min. Detection was performed through UV/Vis at 215 nm.

The standards were injected using the same conditions at concentrations ranging from 2 mM to 20 mM to create a standard curve. Using a spreadsheet application, the peak areas of the standards against their concentration were plotted. Further the slope and intercept of the least square regression line were determined. Checked the line for linearity and discarded the low or high points that are not linear. The test samples were ensured that their absorbance falls within the range of the linear standard concentrations.

Using the Shimadzu LabSolutions Software, the concentration of respective organic acids in a test sample were determined with reference to the standard calibration curve of respective organic acids in terms of difference of sample peak area and the intercept of gradient of organic acids plotted against the slope of standard curve for each of the individual organic acids.

Example 4

Downstream Processing and Product Recovery

As the maximal production of organic acids and complete utilization of glucose was achieved within 48 h of fermentation, a typical production batch was terminated between 44-48 h of fermentation. Further, filtration was performed sequentially by passing the broth through a series of cloth filters with decreasing pore size—from 4 micron up to 0.4 micron—in a plate and frame filtration assembly. The filtered product was then collected in collection tanks. Further processing was done as per product specifications. Following downstream process, the liquid product contained chiefly lactic acid, and small proportions of propionic acid and acetic acid.

(A) Lactic Acid

The filtrate collected in collection tanks was acidified with sulfuric acid for regenerating the lactic acid. Calcium precipitated as calcium sulfate and it was washed. Decolorization was performed by adding activated charcoal to remove organic impurities. Thereafter, concentration of crude lactic acid was carried out in evaporation tanks. The resultant liquid product contained 90-92% lactic acid (Table 1). The production process has been depicted as a flow chart in FIG. 1.

(B) Sodium Lactate

Sodium lactate was prepared through the fermentation process described earlier in the text. The neutralizing agent used for adjusting the pH during fermentation process was sodium carbonate slurry @ 25-50% w/v. After the fermentation cycle was complete at 48 hours, the filtrate was collected in collection tanks and decolorized using activated charcoal. The filtrate was then collected in evaporation tanks where they were concentrated by evaporation. The resultant sodium lactate liquid contained 48-51% lactic acid (Table 1).

(C) Calcium Lactate

Calcium salt of lactic acid was prepared by following methodology. The pH during fermentation process was maintained by periodical addition of calcium carbonate slurry @ 30-50% w/v. Further, the filtrate in collection tank (~3 pH) was neutralized by adding calcium carbonate. The solution was mixed and heated at 80° C. and transferred to a flaking machine to form flakes. The flakes with 50% moisture content were dried in tray dryer and then pulverized to a fine powder. The resultant product contained 60-62% lactic acid, 0.5-1% propionic acid and 1-2% acetic acid (Table 1).

(D) Zinc Lactate

Zinc salt of lactic acid was prepared by following methodology. The pH during fermentation process was maintained by periodical addition of zinc carbonate slurry @ 25-50% w/v. Further, the filtrate in collection tank (~3 pH) was neutralized by adding zinc carbonate. The solution was mixed and heated at 80° C. and transferred to a flaking machine to form flakes. The flakes with ~50% moisture content were dried in tray dryer and then pulverized to a fine powder. The resultant product contained 61-64% lactic acid, 0.2-0.5% propionic acid and 0.5-1% acetic acid (Table 1).

(E) Potassium Lactate

Potassium salt of lactic acid was prepared by following methodology. The pH during fermentation process was maintained by periodical addition of potassium carbonate slurry @40-50% w/v. Further, the filtrate in collection tank (~3 pH) was neutralized by adding potassium carbonate. The solution was mixed and heated at 80° C. and filtered using filter press with cloth filter of 4 microns pore size. The resultant liquid product contained 34-36% lactic acid, 1-1.5% acetic acid and 0.5-1% propionic acid (Table 1).

(F) Magnesium Lactate

Magnesium lactate was prepared by following methodology. The pH during fermentation process was maintained by periodical addition of magnesium carbonate slurry @ 25-30% w/v. Further, the filtrate in collection tank (~3 pH) was neutralized by adding magnesium carbonate. The solution was mixed and heated at 80° C. and transferred to a flaking machine to form flakes. The flakes with ~50% moisture content were dried in tray dryer and then pulverized to a fine powder. The resultant product contained 74-75% lactic acid, 0.5-1% propionic acid and 0.5-1.5% acetic acid (Table 1).

TABLE 1

Technical specifications of high purity organic lactic acid and its salts

| Product name | Lactic acid | Acetic acid | Propionic acid | Other acids | Na | Ca | Zn | K | Mg | Moisture content | Heavy metals |
|---|---|---|---|---|---|---|---|---|---|---|---|
| Lactic acid | 90-92% | NIL | NIL | NIL | NIL | NIL | NIL | NIL | NIL | 8-10% | <20 ppm |
| Sodium lactate | 48-51% | NIL | NIL | NIL | 11-12.5% | NIL | NIL | NIL | NIL | 42-50% | <15 ppm |
| Calcium lactate | 60-62% | 1-2% | 0.5-1% | <1% | NIL | 12-14% | NIL | NIL | NIL | 18-20% | <20 ppm |
| Zinc lactate | 61-64% | 0.5-1% | 0.2-0.5% | <0.1% | NIL | NIL | 23-24.5% | NIL | NIL | 10-12% | <15 ppm |
| Potassium lactate | 34-36% | 1-1.5% | 0.5-1% | <0.1% | NIL | NIL | NIL | 15-17% | NIL | 48-50% | <15 ppm |
| Mg Lactate | 74-75% | 0.5-1% | 0.5-1.5% | <0.1% | NIL | NIL | NIL | NIL | 11-12% | 10-12% | <10 ppm |

INDUSTRIAL APPLICABILITY OF THE INVENTION

"High Purity Organic Lactic acid and its Salts" is an excellent alternative to the chemically synthesised commercial lactic acid. Use of improved microbial strains, naturally extracted glucose and the unique semi-fed-batch fermentation approach yields a high quality natural organic lactic acid in shorter duration, making it time and cost effective and safe for environment and health. Further, it can easily be fortified with different salts to get desired lactates. "High Purity Organic Lactic acid and its Salts" have wide ranging applications in livestock industry as a component of nutritional supplement, providing essential micro- and macronutrients and preventing bacterial and fungal diseases. In food and bakery industry, it may find application as a natural preservative for food preparations like pickles, salads, sauces, beverages, raw or processed meat and bakery goods. It acts as an effective antimicrobial component and Acidifier in Aqua culture industry. It may also be used in pharmaceutical industry as a component of health and mineral supplements, antimicrobial ointments, etc.

REFERENCES

1. Grace Opadoyin Tona. Current and Future Improvements in Livestock Nutrition and Feed Resources. Animal Husbandry and Nutrition. Eds. Banu Yücel and Turgay Taşcin, IntechOpen. (2018) DOI: 10.5772/intechopen.73088.
2. Economou V, Gousia P. Agriculture and food animals as a source of antimicrobial-resistant bacteria. Infect Drug Resist. (2015) 8:49-61. doi: 10.2147/IDR.S55778.
3. Jones F T, Ricke S C. Observations on the history of the development of antimicrobials and their use in poultry feeds. Poult Sci. (2003) 82:613-7. doi: 10.1093/ps/82.4.613.
4. Olsen S J, Ying M, Davis M F, Deasy M, Holland B, Iampietro L, et al. Multidrug-resistant *Salmonella typhimurium* infection from milk contaminated after pasteurization. Emerg Infect Dis. (2004) 10:932-5. doi: 10.3201/eid1005.030484.
5. Dittoe Dana K., Ricke Steven C., Kiess Aaron S. Organic Acids and Potential for Modifying the Avian Gastrointestinal Tract and Reducing Pathogens and Disease. Frontiers in Veterinary Science (2018) 5: 216. Doi: 10.3389/fvets.2018.00216.
6. Dibner J J, Buttin P. Use of organic acids as a model to study the impact of gut microflora on nutrition and metabolism. J Appl Poult Res. (2002) 11: 453-63. doi: 10.1093/japr/11.4.453.
7. Van Immerseel F, Russel J B, Flythe M D, Gantois I, Timbermont L, Pasmans F, Haesebrouck F, Ducatelle R. The use of organic acids to combat *Salmonella* in poulty: a mechanistic explanation of the efficacy. Avian Pathol. (2006) 35:182-8. doi: 10.1080/03079450600711045.
8. Smyser C F, Snoeyenbos G H. Evaluation of organic acids and other compounds as *Salmonella* antagonists in meat and bone meal. Poult Sci. (1979) 58:50-4. doi: 10.3382/ps.0580050.
9. Van Staden J J, Van Der Made H N, Jordaan E. The control of bacterial contamination in carcass meal with propionic acid. Onderstepoort J Vet Res. (1980) 47:77-82.
10. AnyasiTA, JideaniA, EdokpayiJN, Anokwuru C P (2017) Application of organic acids in food preservation edited by Cesar Vargas In book: Organic acids: characteristics, properties and synthesis, Nova Science Publishers. Chapter 1, pp 1-45.
11. Ricke S C. Perspectives on the use of organic acids and short chain fatty acids as antimicrobials. Poult Sci. (2003) 82:632-9. doi: 10.1093/ps/82.4.632.
12. Gang T, Ji L, Zheng L, Jun S (2015) Chinese application no. 201310625005.9. Retrieved from https://patents.google.com/patent/CN104673691.
13. Bin Z (2012) Chinese application no. 201210135060.5. Retrieved from https://patents.google.com/patent/CN102643876.
14. Xusheng J, Xiongya M, Yan S, Zhihong N, Cheng Z, Xudong W (2018) Chinese application no. 201710917450. Retrieved from https://patents.google.com/patent/CN107594135A.
15. Yuanlin L (2017) Chinese application no. 201710307429.9. Retrieved from https://patents.google.com/patent/CN107173556A.
16. Chinese application no. 201280031729.4. Retrieved from https://patents.google.com/patent/CN103781898B.
17. Galkina G V, Illarionova V I, Kuksova E V (2005) Russian application no. 2003118985/13. Retrieved from https://patents.google.com/patent/RU2003118985A.
18. Hidetoshi K, Harumi N (1999) Japanese application no. 6605198. Retrieved from https://patents.google.com/patent/JPH11243867A.
19. Jaeger D, Hering-Giovanola C, Affolter M (2001) Patent application no. PCT/EP2001/003807. Retrieved from https://patents.google.com/patent/WO2001076391A1.
20. Suhwan J (2002) Korean application no. 1020000052784. Retrieved from https://patents.google.com/patent/1020020019992

We claim:

1. A process of producing organic lactic acid or salt thereof, comprising:
   a) co-fermenting by strains of *Lactobacillus delbrueckii* 5356 (MTCC 25858) and *Lactobacillus plantarum* 2083 (MTCC 25859) as a semi-fed batch in fermentation broth in the presence of glucose, obtained through enzymatic hydrolysis of sweet potato as the carbohydrate source, for a period of time for the *Lactobacillus* to consume the glucose and produce organic lactic acid or salt thereof in the fermentation broth;
   b) filtering the fermentation broth to separate and collect the organic lactic acid from the fermentation broth as filtrate;
   c) optionally fortifying the organic lactic acid during co-fermenting or after the organic lactic acid is filtered in b), to produce lactate salt; and
   d) concentrating the organic lactic acid to a concentration of 90% to 92% in the filtrate, or concentrating the lactate salt, if produced.

2. The process as claimed in claim 1, wherein a production medium is used in the fermentation broth and comprises sweet potato extract 18-20% w/v, protein hydrolysate 0.50% w/v, potassium dihydrogen phosphate 0.02% w/v, magnesium sulphate 0.02% w/v, calcium carbonate 3% w/v and zinc sulphate 0.015% w/v and the co-fermenting is carried out for 24 hours at a temperature of 43±2° C. and pH 6.0±0.2 with aeration and impeller speed at 200 rpm.

3. The process as claimed in claim 1, wherein a feed medium is used in the fermentation broth and comprises sweet potato extract 11-16% w/v, protein hydrolysate 0.35% w/v, yeast extract 0.2% w/v, potassium dihydrogen phosphate 0.01% w/v and magnesium sulphate 0.02% w/v, and the co-fermenting is carried out for 20-24 hours at a temperature of 43±2° C. and pH 5.5±0.2 with aeration and impeller speed at 200 rpm.

4. The process as claimed in claim 1, wherein the filtering is performed sequentially by passing the fermentation broth through a series of cloth filters with decreasing pore size in a plate and frame filtration assembly.

5. The process as claimed in claim 1, wherein the fortifying (c) is performed by mixing the organic lactic acid with a) $CaCO_3$ to produce calcium lactate, b) $Na_2CO_3$ to produce sodium lactate, c) $K_2CO_3$ to produce potassium lactate, d) $ZnCO_3$ to produce zinc lactate, or e) $MgCO_3$ to produce magnesium lactate.

6. The process as claimed in claim 5, wherein the resultant lactate salt product comprises 48-51% lactic acid for sodium lactate, 60-62% lactic acid for calcium lactate, 61-64% lactic acid for zinc lactate, 74-75% lactic acid for magnesium lactate, and 34-36% lactic acid for potassium lactate.

7. The process as claimed in claim 1, wherein the organic lactic acid or salt thereof is a clean label and natural product with applications in the livestock industry as a nutritional supplement for animal growth promotion and disease control; as a food preservative in the food industry; as an antimicrobial component and acidifier in the aquaculture industry; as a component of health and mineral supplements in the pharmaceutical industry, or as an antimicrobial ointment.

8. The process as claimed in claim 1, wherein the lactic acid or salt thereof is a nutritional supplement.

9. The process as claimed in claim 1, wherein the lactic acid or salt thereof is a food preservative.

10. The process as claimed in claim 1, wherein the lactic acid or salt thereof is an antimicrobial or antimicrobial ointment.

11. The process as claimed in claim 1, wherein the lactic acid or salt thereof is a mineral supplement.

12. The process as claimed in claim 1, wherein the co-fermenting is performed within 40-48 hours.

13. The process as claimed in claim 1, wherein fortifying the lactic acid produced in the process is performed with calcium, sodium, potassium, zinc or magnesium to produce salts of lactic acid.

* * * * *